(12) United States Patent
Hara et al.

(10) Patent No.: US 7,763,291 B2
(45) Date of Patent: *Jul. 27, 2010

(54) TEA POLYPHENOL COMPOSITION AND METHOD FOR PRODUCING THE SAME

(75) Inventors: Yukihiko Hara, Tokyo (JP); Ryota Seto, Shizuoka (JP)

(73) Assignee: Mitsui Norin Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/631,504

(22) Filed: Dec. 4, 2009

(65) Prior Publication Data

US 2010/0069429 A1 Mar. 18, 2010

Related U.S. Application Data

(62) Division of application No. 11/631,444, filed on Jan. 3, 2007.

(30) Foreign Application Priority Data

Jul. 22, 2004 (JP) ............... 2004-214370

(51) Int. Cl.
A61K 36/82 (2006.01)
C07C 39/12 (2006.01)

(52) U.S. Cl. ...................... 424/729; 568/717

(58) Field of Classification Search ............ None
See application file for complete search history.

(56) References Cited

U.S. PATENT DOCUMENTS

| | | | |
|---|---|---|---|
| 6,063,428 A | 5/2000 | Ekanayake et al. | |
| 6,068,862 A * | 5/2000 | Ishihara et al. | ............... 426/2 |
| 6,268,009 B1 | 7/2001 | Ekanayake et al. | |
| 2003/0077374 A1 | 4/2003 | Ohishi et al. | |
| 2003/0082273 A1 | 5/2003 | Iwasaki et al. | |
| 2004/0065207 A1 | 4/2004 | Oishi et al. | |
| 2005/0186314 A1 | 8/2005 | Sasame et al. | |
| 2005/0196359 A1 | 9/2005 | D'Amelio, Sr. et al. | |
| 2006/0057261 A1 | 3/2006 | Ogura et al. | |

FOREIGN PATENT DOCUMENTS

| | | |
|---|---|---|
| EP | 1504745 | 2/2005 |
| JP | 05139972 | 6/1993 |

OTHER PUBLICATIONS

Goto, et al, Simultaneous analysis of individual catechins and caffeine in green tea, Journal of Chromatography A, 748 (1996) 295-299.

Lin, et al, SUrvey of Catechins, Gallic Acid, and Mehtylxanthines in Green, Oolong, Pu-erh,a nd Black Tea, J. Argic. Food Chem. 1998, 46 3635-3642.

Yoshida, et al, Efficiency of the extraction of catechins from green tea, Food Chemistry (1999) 429-433.

* cited by examiner

*Primary Examiner*—Amy L Clark
(74) *Attorney, Agent, or Firm*—Fish & Associates, PC

(57) ABSTRACT

The objective of the present invention is to provide a tea polyphenol composition that has reduced bitterness and astringency while containing catechins with high purity. The present invention provides a tea polyphenol composition, (A) comprising 85% by weight to 95% by weight of catechins, (B) wherein the catechins contains epigallocatechin gallate and gallocatechin gallate at a ratio of 65% by weight to 80% by weight and (C) wherein the ratio given by (epigallocatechin gallate+gallocatechin gallate)/(epicatechin+catechin+epigallocatechin+gallocatechin+epicatechin gallate+catechin gallate) is from 2 to 4.

14 Claims, No Drawings

TEA POLYPHENOL COMPOSITION AND METHOD FOR PRODUCING THE SAME

This application is a divisional application of U.S. application Ser. No. 11/631,444, filed Jan. 3, 2007, which is a national phase application of International application PCT/JP04/12052, filed Aug. 23, 2004, which claims priority to Japanese application JP 2004-214370.

TECHNICAL FIELD

The present invention relates to a tea polyphenol composition with a taste improved in bitterness, astringency and the like and a production method thereof.

BACKGROUND ART

It has been known that catechins in tea polyphenols have various effects such as an antioxidating effect (Japanese Patent Laid-open No. S59-219384 and Japanese Patent Laid-open No. H1-268683), antimicrobial and bacteriostatic effects (Japanese Patent Laid-open No. H2-276562 and Japanese Patent Laid-open No. H3-246227), an inhibitory activity for cholesterol increase (Japanese Patent Laid-open No. S60-156614), an inhibitory activity for blood pressure increase (Japanese Patent Laid-open No. S63-214183) and an inhibitory activity for blood glucose increase (Japanese Patent Laid-open No. H4-253918).

An increased catechin intake is needed to attain such excellent physiological effects. Tea polyphenol compositions containing high concentrations of catechins have been developed so far.

There have been known, for example, a method of purifying polyphenolic compounds (catechins) to a high purity by contacting with lignocelluloses (refer to Patent Document 1), a method of producing tea catechin compounds in high yields by separating out the unrequired fraction with gel column chromatography using aqueous solutions of hydrophilic organic solvents with concentrations appropriately varied (refer to Patent Document 2), a method of producing highly pure catechins by eliminating caffeine in tea leaves by passing a tea extraction through a liquid chromatography column packed with an adsorbent such as cyclodextrin polymer (refer to Patent Document 3) and the like.

Patent Document 1: Japanese Patent Laid-open No. H7-238078

Patent Document 2: Japanese Patent Laid-open No. H1-175978

Patent Document 3: Japanese Patent Laid-open No. H10-67771

DISCLOSURE OF THE INVENTION

Problems to be Solved by the Invention

In order to increase catechin intake for the purpose of obtaining higher physiological effects, it is effective to ingest a tea polyphenol composition in which the purity of catechins is increased by the above methods.

However, when the tea polyphenol composition with an increased purity of catechins is produced by these methods, bitterness and astringency increase greatly. Moderate bitterness and astringency are crucial in flavor, but excess bitterness and astringency are not generally favorable as a taste.

Accordingly, an object of the present invention is to overcome the above problems and to provide a tea polyphenol composition that has reduced bitterness and astringency while containing catechins in high purity, and an effective production method thereof.

Means for Solving the Problems

The present inventors have undertaken extensive studies to achieve the above objective and found that an excellent tea polyphenol composition that has lower bitterness and astringency while containing catechins in high purity, can be obtained by making the content ratio of ingredients contained in the tea polyphenol composition conform to a specific range. Based on these findings they have completed the present invention.

That is, the present invention is in one aspect a tea polyphenol composition, (A) comprising 85% by weight to 95% by weight of catechins, (B) wherein the catechins contain epigallocatechin gallate and gallocatechin gallate at a ratio of 65% by weight to 80% by weight and (C) wherein the ratio given by (epigallocatechin gallate+gallocatechin gallate)/(epicatechin+catechin+epigallocatechin+gallocatechin+epicatechin gallate+catechin gallate) is from 2 to 4.

The present invention is in another aspect a tea polyphenol composition as described above, wherein the ratio given by (epigallocatechin gallate+epicatechin gallate+gallocatechin gallate+catechin gallate)/(epicatechin+epigallocatechin+gallocatechin+catechin) is from 3 to 7.

The present invention is in a further aspect a tea polyphenol composition as described above, wherein the ratio given by (epigallocatechin gallate+gallocatechin gallate)/(epicatechin+epigallocatechin+gallocatechin+catechin) is from 2 to 6.

The present invention is in yet another aspect a tea polyphenol composition as described above, wherein the catechins contains gallocatechin gallate, gallocatechin, catechin gallate and catechin at a ratio of 2% by weight to 15% by weight.

The present invention is in a still further aspect a tea polyphenol composition as described above, wherein the ratio given by epigallocatechin gallate/(epicatechin+epigallocatechin+epicatechin gallate) is from 2 to 4.

The present invention is in a yet further aspect a tea polyphenol composition as described above, comprising 0.0001% by weight to 1.2% by weight of caffeine.

The present invention is in still another aspect a tea polyphenol composition as described above, comprising 0.0001% by weight to 0.2% by weight of ash.

The present invention is in yet another aspect a tea polyphenol composition as described above, comprising no gallic acid.

The present invention is in a still further aspect a method for producing the tea polyphenol compositions as described above performed in the following steps 1) to 3):

1) A step in which tea components containing the catechins are extracted from tea leaves with hot water and further extracted with an organic solvent to provide a tea extract;
2) A step in which the tea extract is fed to a synthetic adsorption resin; and
3) A step in which the synthetic adsorption resin is washed with a 5% to 15% aqueous alcohol solution and then the tea catechins is eluted by passing a 30% to 50% aqueous alcohol solution through the resin.

Effects of the Invention

The tea polyphenol composition of the present invention contains a higher catechin purity, so that it can more effectively exert excellent physiological effects of catechins, for example, an antioxidating effect, antimicrobial and bacteriostatic effects, an inhibitory activity for cholesterol increase, an inhibitory activity for blood pressure increase, an inhibitory effect against blood glucose increase and the like.

In addition, the tea polyphenol composition of the present invention exhibits an excellent improved taste, with reduced bitterness and astringency.

Furthermore, by the method of the present invention, such a tea polyphenol composition can be efficiently produced.

BEST MODE FOR CARRYING OUT THE INVENTION

The present invention is in one aspect a tea polyphenol composition, wherein (A) comprising 85% by weight to 95% by weight of catechins, (B) wherein the catechins contains epigallocatechin gallate and gallocatechin gallate at a ratio of 65% by weight to 80% by weight and (C) wherein the ratio given by (epigallocatechin gallate+gallocatechin gallate)/ (epicatechin+catechin+epigallocatechin+gallocatechin+epicatechin gallate+catechin gallate) is from 2 to 4.

The "catechins" in the present invention means a collective term including epigallocatechin gallate (hereinafter referred to as EGCg), epigallocatechin (hereinafter referred to as EGC), epicatechin gallate (hereinafter referred to as ECg), epicatechin (hereinafter referred to as EC), gallocatechin gallate (hereinafter referred to as GCg), gallocatechin (hereinafter referred to as GC), catechin gallate (hereinafter referred to as Cg) and catechin (hereinafter referred to as C). Each of catechins described here may be either (+)-form or (−)-form, and (−)-EGCg, (−)-EGC, (−)-ECg, (−)-EC, (−)-GCg, (−)-GC, (−)-Cg and (+)-C are preferable.

The tea polyphenol composition of the present invention comprises in another aspect the above-described catechins in a content of 85% by weight to 95% by weight, preferably 85.5% by weight to 94.5% by weight, more preferably 86% by weight to 94% by weight and further more preferably 86.5% by weight to 93.5% by weight. When the content of the catechins is within this range, a large amount of catechins can be readily ingested and the natural taste of tea can be obtained. The concentration of the catechins described here is defined based on the total amount of the eight kinds of compounds, EGCg, EGC, ECg, EC, GCg, GC, Cg and C.

In one aspect, the tea polyphenol composition of the present invention, in order for the excellent physiological effects of the catechins to be exerted more effectively, out of all the catechins the ratio of EGCg and GCg is required to be from 65% by weight to 80% by weight, preferably from 66% by weight to 79% by weight, more preferably from 67% by weight to 79% by weight and further more preferably from 68% by weight to 78.5% by weight.

In another aspect of the present invention, the value obtained by dividing the sum of the concentrations of EGCg and GCg by the sum of the concentrations of EC, C, EGC, GC, ECg and Cg is preferably from 2 to 4, more preferably from 2.1 to 3.9, further more preferably from 2.2 to 3.8 and most preferably from 2.3 to 3.7 in order to improve the taste of the catechins such as bitterness and astringency.

In a further aspect of the present invention, the value obtained by dividing the sum of concentrations of EGCg, ECg, GCg and Cg (catechin gallate) by the sum of the concentrations of EC, EGC, GC and C (non-gallated catechins) is preferably from 3 to 7, more preferably from 3.1 to 6.8, further more preferably from 3.1 to 6.6 and most preferably from 3.2 to 6.4. This range is preferred because the excellent physiological effects of the catechins are readily exerted and because tastes such as bitterness and astringency are reduced.

In a still further aspect of, in the present invention, the value given by dividing the sum of the concentrations of EGCg and GCg by the sum of the concentrations of EC, EGC, GC and C (non-gallated catechins) is preferably from 2 to 6, more preferably from 2.5 to 5.9, further more preferably from 2.8 to 5.8 and most preferably from 2.9 to 5.6 in order to improve the taste of the catechins such as bitterness and astringency.

In yet a further aspect of the present invention, the total content of GCg, GC, Cg and C (non-epimerized catechins) in the catechins is preferably from 2% by weight to 15% by weight, more preferably from 2.2% by weight to 13% by weight, further more preferably from 2.5% by weight to 11% by weight and most preferably from 2.7% by weight to 10.4% by weight in order to improve the flavor.

In the tea polyphenol composition of the present invention, the weight ratio given by EGCg/(EC+EGC+ECg) is preferably from 2 to 4, more preferably from 2.2 to 3.9 and further more preferably from 2.1 to 3.8 in order to improve the taste of the catechins such as bitterness and astringency.

In the tea polyphenol composition of the present invention, the content of caffeine is preferably from 0.0001% by weight to 1.2% by weight and more preferably from 0.001% by weight to 1.2% by weight. If the content of caffeine exceeds 1.2% by weight, dizziness, insomnia, palpitation, nausea or other symptoms could be caused due to the strong physiological effects of caffeine under some conditions of intake and of the person who takes it, and thus such a high caffeine content is not preferred.

In the tea polyphenol composition of the present invention, the content of ash is preferably from 0.0001% by weight to 0.2% by weight and more preferably from 0.001% by weight to 0.2% by weight in order to improve the taste such as astringency and bitterness.

In the present invention, it is preferred that gallic acid is not present in order to exert the excellent physiological effects of the catechins more effectively.

In the present invention, the composition having all the requirements described in the above and with improved tastes such as astringency and bitterness is preferred, and in particular the composition with a combination of the preferred ranges is more preferred.

The tea polyphenol compositions described above, can be produced, for example, by the method of the present invention.

That is, the present invention is in one aspect a method for producing the tea polyphenol compositions described herein performed in the following steps 1) to 3):

1) A step in which tea components containing the catechins are extracted from tea leaves with hot water and further extracted with an organic solvent to provide a tea extract;

2) A step in which the tea extract is fed to a synthetic adsorption resin;

3) A step in which after the synthetic adsorption resin is washed with a 5% to 15% aqueous alcohol solution, the tea catechins is eluted by passing a 30% to 50% aqueous alcohol solution through the resin.

The "tea polyphenol" in the present invention means an extract containing polyphenol(s) extracted from tea leaves or a purified polyphenolic compound.

Here, "tea leaves" means leaves derived from a tea plant belonging to Theaceae (*Camellia sinensis*) and may include, regardless of being fermented or not, any one of fermented teas such as ready-made black tea and puer tea, semi-fermented tea such as oolong tea and Pao Chung tea and non-fermented tea such as green tea, pan-roasted green tea and roasted tea and it may be a mixture of two or more kinds of these.

The amount of the polyphenol of the present invention may be determined by the colorimetric quantitative analysis method using iron tatarate, but measurement with reversed phase high performance liquid chromatography is preferred to determine the composition of the tea polyphenol in detail.

The tea leaves used in the present invention may be raw or dried, but dried leaves are preferably used. When dried material is used, the tea leaves are dried and then crushed if necessary to provide the raw material for the extraction step. For example, such material can be prepared by drying the raw tea leaves followed by crushing or by cutting the raw tea leaves into small pieces followed by drying.

The present invention comprises in one aspect the three steps, 1) to 3) mentioned above.

The first step is a step in which tea components containing the catechins are extracted from the tea leaves with hot water and then further extracted with an organic solvent to provide a tea extract (extraction step).

In this extraction step, the tea components containing the catechins are at first extracted from the above-described tea leaves with hot water. There is no defined limit for the temperature of the hot water used here as long as it is 100° C. or lower under atmospheric pressure. The temperature is preferably from 60° C. to 100° C., more preferably from 70° C. to 90° C. and most preferably from 80° C. to 85° C. If this extraction is done at a temperature over 100° C., structural conversions such as isomer polymerization of the catechins could take place, and thus such a high temperature is unfavorable, whereas if extracted below 60° C., the catechins are not fully extracted, thus such a low temperature is unfavorable. When extraction is performed under positive pressure, the catechins can be extracted at a temperature lower than that under atmospheric pressure, and the temperature on extraction may be adjusted as appropriate for the pressure applied. The amount of hot water for extraction from the tea leaves is, although not particularly limited to, preferably three to ten times, more preferably five to seven times that of the tea leaves by weight. If the amount of hot water used is less than three times that of the tea leaves by weight, the catechins cannot be sufficiently extracted, whereas use of hot water in an amount of more than ten times that of the tea leaves does not particularly improve the extraction efficiency. Extraction with hot water may be performed either only once or repeatedly two or more times but it is preferred to extract twice. When extraction is performed twice, the amounts of hot water used are, although not particularly limited to, preferably seven times that of the tea leaves by weight in the first extraction and five times that of the tea leaves by weight in the second extraction.

The liquid extract obtained by the above-described extraction with hot water is cooled once. The temperature on cooling is preferably 50° C. or lower, more preferably 30° C. or lower and most preferably 15° C. or lower. If the temperature on cooling exceeds 50° C., insoluble components cannot be fully removed in centrifugal filtration in a later step, and thus such a condition is not favored.

Next, the cooled extracted liquid is concentrated. The method for concentration may be any of methods generally used, for example, vacuum concentration method, atmospheric concentration method, heating concentration method, batch concentration method, membrane concentration method and circulation concentration method. The membrane concentration method, in particular, the membrane concentration method with a reverse osmosis (RO) membrane is preferably used. Filter filtration, centrifugal filtration or the like may be run prior to concentration without any problem.

In the first step, as described above, the tea components containing the catechins are extracted from the tea leaves with hot water, and the liquid extract obtained is preferably cooled to and then concentrated, thereby yielding a concentrated liquid, which is further extracted with an organic solvent.

The organic solvent used here includes an organic solvent that can dissolve the tea polyphenol, for example, acetonitrile, methanol, ethanol, ethyl acetate, acetone, methyl ethyl ketone, methyl isobutyl ketone, tetrahydrofuran or dioxane, hydrous organic solvent thereof and a mixed solvent of these organic solvents. Among these, ethyl acetate is preferably used. The amount of the organic solvent is preferably a half to five times, more preferably one to three times, most preferably one and a half to two times that of the concentrated liquid by volume. If the volume of the organic solvent is less than a half of the concentrated liquid, the catechins cannot be fully extracted, whereas if the volume exceeds five times that of the concentrated liquid, the extraction efficiency is not particularly improved.

Then the organic solvent layer obtained is concentrated. The concentration method used here may be any of methods generally used including, for example, vacuum concentration method, atmospheric concentration method, heating concentration method, batch concentration method, membrane concentration method or circulation concentration method. A combination of any of the above-mentioned methods may be also used, and a combination of vacuum concentration method, heating concentration method and circulation concentration method is particularly preferred.

The above-described concentrated liquid is dried to obtain a tea extract (crude tea extract). The drying method is, although not particularly limited to, preferably spray drying method, freeze drying method, vacuum drying method or the like. A commercial product may be also used as a crude tea extract without any problem.

The second step is a step to feed the tea extract (crude tea extract) obtained in the first step to a synthetic adsorption resin.

In this second step, at first, the crude tea extract obtained is dissolved preferably in a 5% to 15% aqueous alcohol solution, more preferably in a 10% aqueous alcohol solution and further more preferably in a 10% aqueous methanol solution, and then the resultant solution is fed to a synthetic adsorption resin to adsorb tea extract components.

The synthetic adsorption resin used is preferably crosslinked styrenic type, including, for example, HP-20 (Diaion, manufactured by Mitsubishi Chemical Corporation), Sepabeads (manufactured by Mitsubishi Chemical Corporation), Amberlite (manufactured by Organo Corporation), Shodex (manufactured by Showa Denko K.K.) and Sephadex (manufactured by Pharmacia Fine Chemicals AB).

The third step is a step in which the synthetic adsorption resin is washed with a 5% to 15% aqueous alcohol solution and then the tea catechins are eluted by passing a 30% to 50% aqueous alcohol solution through the resin.

In this third step, wherein the catechins are eluted by passing a 30 to 50% aqueous alcohol solution, unadsorbed components are washed out before the elution with the 30% to 50% aqueous alcohol solution.

That is, the synthetic adsorption resin is at first washed with a 5% to 15% aqueous alcohol solution to wash out the unadsorbed components. The concentration of the aqueous alcohol solution used here may be from 5% to 15% and preferably 10%. A volume of 50 L or more is sufficient as the amount of the aqueous alcohol solution to be passed through a column with a capacity of 300 L.

After this washing, a 30% to 50% aqueous alcohol solution is passed through to elute the tea catechins. The kind of the aqueous alcohol solution used here is, although not restricted, preferably an aqueous methanol solution. The concentration of the aqueous alcohol solution may be from 30% to 50%, and is preferably from 35% to 45% and more preferably 40%. Therefore, a 40% aqueous methanol solution is preferably used to elute the tea catechins. The volume of the aqueous alcohol solution passed through a column with a capacity of 300 L is 100 L or more and preferably 280.+−0.56 L.

Finally, it is preferred to remove insoluble components such as caffeine by washing with an aqueous alcohol solution. The kind of the aqueous alcohol solution used here is, although not restricted, preferably an aqueous methanol solution. The concentration of the aqueous alcohol solution may be from 50% to 100% and is preferably from 60% to 80% and more preferably 70%. The volume of the aqueous alcohol passed through a column with a capacity of 300 L is 100 L or more, preferably 400 L or more and further preferably 600 L or more.

It is advisable that recovery of the tea catechin fraction starts at a time when the content of (−)-EGCg has reached a level twice or more, preferably five times or more, as high as that of (−)-EGC and ends at a time when the content of (−)-EGCg has reached a level lower than that of (−)-ECg or at a time when the content of caffeine becomes 5%, preferably 1%. If the timing to start the recovery is set earlier than the above timing, the content of (−)-EGCg decreases, whereas if the timing to end the recovery is later than the above timing, the content of (−)-EGCg decreases and the content of caffeine increases.

The tea polyphenol composition of the present invention is obtained by concentrating and drying the tea catechin fraction obtained in the above steps. The concentration method may be any of the methods generally used including, for example, vacuum concentration method, atmospheric concentration method, heating concentration method, batch concentration method, membrane concentration method, circulation concentration method or the like. A combination of a any of the above-mentioned concentration methods may be also used and a combination of vacuum concentration method, heating concentration method and circulation concentration method is preferred in particular. There is no particular set drying method, but spray drying method, freeze drying method, vacuum drying method and the like may be favorably used.

In the tea polyphenol composition hereby obtained, tastes peculiar to the catechins, such as bitterness and astringency, are substantially reduced.

Furthermore, this tea polyphenol composition can be expected to contribute to imparting the primary effects of the polyphenol, for example, physiological functions, such as antioxidative effect, antimicrobial and bacteriostatic effects, inhibitory action on cholesterol increase, inhibitory action on blood pressure increase and an inhibitory action on blood glucose increase, without fear of the negative effects of caffeine described hereinafter because the composition has a high content of the tea catechins with a gallate group and almost no caffeine or gallic acid content. Caffeine is known to have physiological activities such as an excitatory activity on the central nervous system, a positive inotropic effect and a diuretic effect. Under some conditions of the intake and of the person who takes it, dizziness, insomnia, palpitation, nausea or other symptoms might be caused due to strong physiological effects of caffeine, so that people hypersensitive to caffeine may regard intake of caffeine problematic.

Since the tea polyphenol composition of the present invention is chemically, physically and biologically very stable, the field of its application is not limited, and it can be added to, for example, food and drink, pharmaceuticals, quasi drugs, cosmetics, textiles or the like. According to the application, the product of the present invention may be used together with a vitamin such as tocopherol or vitamin C, an antimicrobial or bactericidal agent, a coloring matter, an aroma agent, a bulking agent, a coating agent or the like.

EXAMPLE

Examples, comparative examples and test examples are illustrated below to describe the present invention in more detail. However, the present invention is not restricted by these examples.

Example 1

Production of Product 1 in the Present Invention

Two hundred and seventy kilograms of dried green tea leaves was subjected to extraction with 1890 L of hot water at 80° C. and then to additional extraction with 1350 L of hot water at 80° C. This liquid extract was cooled to a temperature of 15° C. or lower, and then concentrated using an RO membrane to obtain 500 L of a concentrated liquid. This concentrated liquid was extracted with 1000 L of ethyl acetate, the ethyl acetate layer was concentrated to 75 kg, and the concentrated solution was dried to obtain 15 kg of a crude tea extract.

Twelve kilograms of the crude tea extract hereby obtained was used as a raw material. This tea extract was dissolved in 22 L of a 10% aqueous methanol solution and the resultant solution was added to 300 L of a crosslinked styrenic synthetic adsorption resin (HP-20, manufactured by Mitsubishi Chemical Corporation) to adsorb components in the tea extract.

After the unadsorbed components were removed by passing 280 L of a 10% aqueous methanol solution through the resin, the tea catechin fraction was eluted with 280 L of a 40% aqueous methanol solution. Subsequently insoluble components were washed out and removed by passing 600 L of a 70% aqueous methanol solution through the resin. Approximately 240 L of a tea catechin fraction was recovered. This fraction was subjected to circulation concentration with a centrifugal thin-film evaporator (manufactured by Okawara Mfg. Co., Ltd.) to obtain approximately 20 L of a concentrated liquid. This concentrated liquid was spray-dried with a spray dryer (manufactured by Niro A/S) to obtain 4.8 kg of a tea polyphenol composition, which was designated as Product 1 in the present invention.

Ingredients in the tea polyphenol composition (Product 1 of present invention) hereby obtained were analyzed with high performance liquid chromatography under conditions given below. Composition of this tea polyphenol composition is shown in Table 1.

[Condition of High Performance Liquid Chromatography]

Column: Mightysil (manufactured by Kanto Chemical Co., Inc.)

Mobile phase solution A: A solution containing acetonitrile and aqueous phosphoric acid solution with a ratio of 10:400

Mobile phase solution B: A solution containing methanol, acetonitrile and aqueous phosphoric acid solution with a ratio of 200:10:400

Detection: UV at 230 nm

Column temperature: 40° C.

Sample temperature: room temperature

Sample volume: 10.mu.L

Flow rate: 1 mL/min

Example 2

Production of Product 2 in the Present Invention

Two hundred and seventy kilograms of dried green tea leaves was subjected to extraction with 1890 L of hot water at 80° C. and then to additional extraction with 1350 L of hot water at 80° C. This liquid extract was cooled to a temperature of 15° C. or lower, and then concentrated using an RO membrane to obtain 500 L of a concentrated liquid. This concentrated liquid was extracted with 1000 L of ethyl acetate, the ethyl acetate layer was concentrated to 75 kg, and the concentrated solution was dried to obtain 15 kg of a crude tea extract.

Twelve kilograms of the crude tea extract hereby obtained was used as a raw material. This tea extract was dissolved in 22 L of a 10% aqueous methanol solution and the resultant solution was added to 300 L of a crosslinked styrenic synthetic adsorption resin (HP-20, manufactured by Mitsubishi Chemical Corporation) to adsorb components in the tea extract.

After the unadsorbed components were removed by passing 280 L of a 10% aqueous methanol solution through the resin, the tea catechin fraction was eluted with 280 L of a 35% aqueous methanol solution. Subsequently insoluble components were washed out and removed by passing 600 L of a 70% aqueous methanol solution through the resin. Approximately 240 L of a tea catechin fraction was recovered. This fraction was subjected to circulation concentration with a centrifugal thin-film evaporator (manufactured by Okawara Mfg. Co., Ltd.) to obtain approximately 20 L of a concentrated liquid. This concentrated liquid was spray-dried with a spray dryer (manufactured by Niro A/S) to obtain 4.8 kg of a tea polyphenol composition, which was designated as Product 2 in the present invention.

Ingredients in the tea polyphenol composition (Product 2 in the present invention) hereby obtained were analyzed similarly to Example 1. The results are given in Table 1.

Example 3

Production of Product 3 in the Present Invention

Two hundred and seventy kilograms of dried green tea leaves was subjected to extraction with 1890 L of hot water at 80° C. and then to additional extraction with 1350 L of hot water at 80° C. This liquid extract was cooled to a temperature of 15° C. or lower, and then concentrated using an RO membrane to obtain 500 L of a concentrated liquid. This concentrated liquid was extracted with 1000 L of ethyl acetate, the ethyl acetate layer was concentrated to 75 kg, and the concentrated solution was dried to obtain 15 kg of a crude tea extract.

Twelve kilograms of the crude tea extract hereby obtained was used as a raw material. This tea extract was dissolved in 22 L of a 10% aqueous methanol solution and the resultant solution was added to 300 L of a crosslinked styrenic synthetic adsorption resin (HP-20, manufactured by Mitsubishi Chemical Corporation) to adsorb components in the tea extract.

After the unadsorbed components were removed by passing 280 L of a 5% aqueous methanol solution through the resin, the tea catechin fraction was eluted with 280 L of a 35% aqueous methanol solution. Subsequently insoluble components were washed out and removed by passing 600 L of a 70% aqueous methanol solution through the resin. Approximately 240 L of a tea catechin fraction was recovered. This fraction was subjected to circulation concentration with a centrifugal thin-film evaporator (manufactured by Okawara Mfg. Co., Ltd.) to obtain approximately 20 L of a concentrated liquid. This concentrated liquid was spray-dried with a spray dryer (manufactured by Niro A/S) to obtain 4.8 kg of a tea polyphenol composition, which was designated as Product 3 in the present invention.

Ingredients in the tea polyphenol composition (Product 3 in the present invention) hereby obtained were analyzed similarly to Example 1. The results are given in Table 1.

Example 4

Production of Product 4 in the Present Invention

Two hundred and seventy kilograms of dried green tea leaves was subjected to extraction with 1890 L of hot water at 80° C. and then to additional extraction with 1350 L of hot water at 80° C. This liquid extract was cooled to a temperature of 15° C. or lower, and then concentrated using an RO membrane to obtain 500 L of a concentrated liquid. This concentrated liquid was extracted with 1000 L of ethyl acetate, the ethyl acetate layer was concentrated to 75 kg, and the concentrated solution was dried to obtain 15 kg of a crude tea extract.

Twelve kilograms of the crude tea extract hereby obtained was used as a raw material. This tea extract was dissolved in 22 L of a 10% aqueous methanol solution and the resultant solution was added to 300 L of a crosslinked styrenic synthetic adsorption resin (HP-20, manufactured by Mitsubishi Chemical Corporation) to adsorb components in the tea extract.

After the unadsorbed components were removed by passing 280 L of a 10% aqueous methanol solution through the resin, the tea catechin fraction was eluted with 280 L of a 45% aqueous methanol solution. Subsequently insoluble components were washed out and removed by passing 600 L of a 65% aqueous methanol solution through the resin. Approximately 240 L of a tea catechin fraction was recovered. This fraction was subjected to circulation concentration with a centrifugal thin-film evaporator (manufactured by Okawara Mfg. Co., Ltd.) to obtain approximately 20 L of a concentrated liquid. This concentrated liquid was spray-dried with a spray dryer (manufactured by Niro A/S) to obtain 4.8 kg of a tea polyphenol composition, which was designated as Product 4 in the present invention.

Ingredients in the tea polyphenol composition (Product 4 in the present invention) hereby obtained were analyzed similarly to Example 1. The results are given in Table 1.

Example 5

Production of Product 5 in the Present Invention

Two hundred and seventy kilograms of dried green tea leaves was subjected to extraction with 1890 L of hot water at 80° C. and then to additional extraction with 1350 L of hot water at 80° C. This liquid extract was cooled to a temperature of 15° C. or lower, and then concentrated using an RO membrane to obtain 500 L of a concentrated liquid. This concentrated liquid was extracted with 1000 L of ethyl acetate, the ethyl acetate layer was concentrated to 75 kg, and the concentrated solution was dried to obtain 15 kg of a crude tea extract.

Twelve kilograms of the crude tea extract hereby obtained was used as a raw material. This tea extract was dissolved in 22 L of a 10% aqueous methanol solution and the resultant solution was added to 300 L of a crosslinked styrenic synthetic adsorption resin (HP-20, manufactured by Mitsubishi Chemical Corporation) to adsorb components in the tea extract.

After the unadsorbed components were removed by passing 280 L of a 15% aqueous methanol solution through the resin, the tea catechin fraction was eluted with 280 L of a 35% aqueous methanol solution. Subsequently insoluble components were washed out and removed by passing 600 L of a 70% aqueous methanol solution through the resin. Approximately 240 L of a tea catechin fraction was recovered. This fraction was subjected to circulation concentration with a centrifugal thin-film evaporator (manufactured by Okawara Mfg. Co., Ltd.) to obtain approximately 20 L of a concentrated liquid. This concentrated liquid was spray-dried with a spray dryer (manufactured by Niro A/S) to obtain 4.8 kg of a tea polyphenol composition, which was designated as Product 5 in the present invention.

Ingredients in the tea polyphenol composition (Product 5 in the present invention) hereby obtained were analyzed similarly to Example 1. The results are given in Table 1.

Example 6

Production of Product 6 in the Present Invention

Two hundred and seventy kilograms of dried green tea leaves was subjected to extraction with 1890 L of hot water at 80° C. and then to additional extraction with 1350 L of hot water at 80° C. This liquid extract was cooled to a temperature of 15° C. or lower, and then concentrated using an RO membrane to obtain 500 L of a concentrated liquid. This concentrated liquid was extracted with 1000 L of ethyl acetate, the ethyl acetate layer was concentrated to 75 kg, and the concentrated solution was dried to obtain 15 kg of a crude tea extract.

Twelve kilograms of the crude tea extract hereby obtained was used as a raw material. This tea extract was dissolved in 22 L of a 10% aqueous methanol solution and the resultant solution was added to 300 L of a crosslinked styrenic synthetic adsorption resin (HP-20, manufactured by Mitsubishi Chemical Corporation) to adsorb components in the tea extract.

After the unadsorbed components were removed by passing 280 L of a 15% aqueous methanol solution through the resin, the tea catechin fraction was eluted with 280 L of a 40% aqueous methanol solution. Subsequently insoluble components were washed out and removed by passing 600 L of a 65% aqueous methanol solution through the resin. Approximately 240 L of a tea catechin fraction was recovered. This fraction was subjected to circulation concentration with a centrifugal thin-film evaporator (manufactured by Okawara Mfg. Co., Ltd.) to obtain approximately 20 L of a concentrated liquid. This concentrated liquid was spray-dried with a spray dryer (manufactured by Niro A/S) to obtain 4.8 kg of a tea polyphenol composition, which was designated as Product 6 in the present invention.

Ingredients in the tea polyphenol composition (Product 6 in the present invention) hereby obtained were analyzed similarly to Example 1. The results are given in Table 2.

Example 7

Production of Product 7 in the Present Invention

Two hundred and seventy kilograms of dried green tea leaves was subjected to extraction with 1890 L of hot water at 80° C. and then to additional extraction with 1350 L of hot water at 80° C. This liquid extract was cooled to a temperature of 15° C. or lower, and then concentrated using an RO membrane to obtain 500 L of a concentrated liquid. This concentrated liquid was extracted with 1000 L of ethyl acetate, the ethyl acetate layer was concentrated to 75 kg, and the concentrated solution was dried to obtain 15 kg of a crude tea extract.

Twelve kilograms of the crude tea extract hereby obtained was used as a raw material. This tea extract was dissolved in 22 L of a 10% aqueous methanol solution and the resultant solution was added to 300 L of a crosslinked styrenic synthetic adsorption resin (HP-20, manufactured by Mitsubishi Chemical Corporation) to adsorb components in the tea extract.

After the unadsorbed components were removed by passing 280 L of a 15% aqueous methanol solution through the resin, the tea catechin fraction was eluted with 280 L of a 40% aqueous methanol solution. Subsequently insoluble components were washed out and removed by passing 600 L of a 75% aqueous methanol solution through the resin. Approximately 240 L of a tea catechin fraction was recovered. This fraction was subjected to circulation concentration with a centrifugal thin-film evaporator (manufactured by Okawara Mfg. Co., Ltd.) to obtain approximately 20 L of a concentrated liquid. This concentrated liquid was spray-dried with a spray dryer (manufactured by Niro A/S) to obtain 4.8 kg of a tea polyphenol composition, which was designated as Product 7 in the present invention.

Ingredients in the tea polyphenol composition (Product 7 in the present invention) hereby obtained were analyzed similarly to Example 1. The results are given in Table 2.

Comparative Examples 1 to 3

Commercial products were used.

That is, commercial polyphenol preparations "Polyphenon 70A" (manufactured by Mitsui Norin Co., Ltd.), "Polyphenon 60B" (manufactured by Mitsui Norin Co., Ltd.) and pure epigallocatechin gallate were used in Comparative Example 1 (Comparative Product 1), Comparative Example 2 (Comparative Product 2) and Comparative Example 3 (Comparative Product 3), respectively.

Ingredients in these tea polyphenol compositions (Comparative Products 1 to 3) were analyzed similarly to Example 1. The results are shown in Table 2.

Test Example 1

Sensory Evaluation of the Tea Polyphenol Compositions for Bitterness and Astringency Bitterness and astringency of the tea polyphenol compositions obtained in Examples 1 to 7 and Comparative Examples 1 to 3 were examined according to the following test method. The results are shown in Tables 1 and 2.

[Test Method]

Sensory evaluation was conducted with ten men and women randomly chosen as panelists.

Each sample of Products 1 to 7 in the present invention obtained in the examples and Comparative Products 1 to 3 was added to 800 g of ion-exchanged water so that the catechin content was 1 g. To this solution, 0.3 g of sodium ascorbate and an appropriate amount of a 5% aqueous sodium bicarbonate solution were added to adjust pH to 6.2 and the solution was further diluted with ion-exchanged water to adjust the total amount to 1000 g to prepare a test solution. The products in the present invention were compared with the comparative products to evaluate whether the bitterness and astringency were reduced or not. Evaluation of bitterness and astringency was rated in five levels described below. After evaluation of one sample of the test and comparative solutions, the mouth was rinsed with warm water, and next evaluation was conducted after 30 min or later.

[Rating Criteria for Evaluation]

| | |
|---|---|
| Very strong bitterness and astringency | 5 |
| Strong bitterness and astringency | 4 |
| Weak bitterness and astringency | 3 |
| Some bitterness and astringency | 2 |
| No bitterness and astringency | 1 |

TABLE 1

| | | Product 1 in present invention | Product 2 in present invention | Product 3 in present invention | Product 4 in present invention | Product 5 in present invention |
|---|---|---|---|---|---|---|
| EGCg | % by weight | 64.6 | 61.1 | 59.7 | 66.9 | 61.2 |
| EC | % by weight | 9.7 | 11.2 | 11.5 | 9.0 | 9.4 |
| EGC | % by weight | 5.0 | 5.0 | 7.6 | 4.5 | 1.8 |
| ECg | % by weight | 5.8 | 5.9 | 5.4 | 4.5 | 9.1 |
| GC | % by weight | 0.5 | 0.3 | 0.6 | 0.3 | 0.2 |
| GCg | % by weight | 6.3 | 3.7 | 3.7 | 3.7 | 7.5 |
| Cg | % by weight | 0.3 | 0.2 | 0.2 | 0.0 | 0.5 |
| C | % by weight | 1.3 | 1.5 | 1.7 | 1.1 | 0.9 |
| All the catechins | % by weight | 93.5 | 88.9 | 90.4 | 90.0 | 90.6 |
| (EGCg + GCg)/All the catechins | % by weight | 75.83 | 72.89 | 70.13 | 78.44 | 75.83 |
| (EGCg + GCg)/(EC + EGC + ECg + C + GC + Cg) | | 3.14 | 2.69 | 2.35 | 3.64 | 3.14 |
| (EGCg + ECg + GCg + Cg)/(EC + EGC + C + GC) | | 4.67 | 3.94 | 3.22 | 5.04 | 6.37 |
| (EGCg + GCg)/(EC + EGC + C + GC) | | 4.30 | 3.60 | 2.96 | 4.74 | 5.59 |
| (GC + GCg + C + Cg)/All the catechins | % by weight | 8.98 | 6.41 | 6.86 | 5.67 | 10.04 |
| EGCg/(EC + EGC + ECg) | | 3.15 | 2.76 | 2.44 | 3.72 | 3.01 |
| Caffeine | % by weight | 0.6 | 0.5 | 0.9 | 0.4 | 0.4 |
| Ash | % by weight | 0.1 | 0.1 | 0.1 | 0.1 | 0.1 |
| Gallic acid | % by weight | 0.0 | 0.0 | 0.0 | 0.0 | 0.0 |
| Rating of bitterness and astringency | | 2.4 | 2.1 | 2.2 | 2.4 | 2.3 |

TABLE 2

| | | Product 6 in present invention | Product 7 in present invention | Comparative Product 1 | Comparative Product 2 | Comparative Product 3 |
|---|---|---|---|---|---|---|
| EGCg | % by weight | 67.1 | 61.1 | 56.1 | 34.9 | 100.0 |
| EC | % by weight | 11.0 | 9.1 | 2.8 | 4.7 | — |
| EGC | % by weight | 5.2 | 3.3 | 3.6 | 8.4 | — |
| ECg | % by weight | 5.3 | 7.5 | 12.6 | 8.9 | — |
| GC | % by weight | 0.1 | 0.3 | 0.9 | 1.4 | — |
| GCg | % by weight | 1.5 | 7.4 | 3.4 | 1.5 | — |
| Cg | % by weight | 0.0 | 0.4 | 0.4 | 0.4 | — |
| C | % by weight | 0.9 | 1.2 | 0.8 | 0.7 | — |
| All the catechins | % by weight | 91.1 | 90.3 | 80.6 | 60.9 | 100.0 |
| (EGCg + GCg)/All the catechins | % by weight | 75.30 | 75.86 | 73.82 | 59.77 | — |
| (EGCg + GCg)/(EC + EGC + ECg + C + GC + Cg) | | 3.05 | 3.14 | 2.82 | 1.49 | — |
| (EGCg + ECg + GCg + Cg)/(EC + EGC + C + GC) | | 4.30 | 5.50 | 8.95 | 3.01 | — |
| (EGCg + GCg)/(EC + EGC + C + GC) | | 3.99 | 4.93 | 7.35 | 2.39 | — |
| (GC + GCg + C + Cg)/All the catechins | % by weight | 2.74 | 10.30 | 6.82 | 6.57 | — |
| EGCg/(EC + EGC + ECg) | | 3.12 | 3.07 | 2.95 | 1.59 | — |
| Caffeine | % by weight | 0.7 | 0.4 | 0.4 | 0.4 | — |
| Ash | % by weight | 0.1 | 0.1 | 0.1 | 0.1 | — |
| Gallic acid | % by weight | 0.0 | 0.0 | 0.0 | 0.0 | — |
| Rating of bitterness and astringency | | 2.4 | 2.3 | 4.3 | 4.5 | 4.5 |

As shown in Tables 1 and 2, it is clear that Products 1 to 7 in the present invention are less bitter and astringent than Comparative Products 1 to 3.

What is claimed is:

1. A tea polyphenol composition having reduced bitterness and astringency, comprising:
   a plurality of at least seven distinct catechins, wherein the catechins are selected from the group consisting of EGCg, GCg, EC, C, EGC, GC, ECg, and Cg;
   wherein 85 wt % to 95 wt % of the tea polyphenol composition is comprised of the plurality of catechins;
   wherein at least 70 wt % of the tea polyphenol composition is comprised of EC, C, and EGCg together;
   wherein EC and C together account for at least 11% of the plurality of distinct catechins, and wherein the tea polyphenol composition is obtained by the process comprising the steps of:
   (a) subjecting tea leaves to extraction with hot water at a temperature of from 60° C. to 100° C. to form an aqueous extract;
   (b) cooling the aqueous extract to a temperature of 50° C. or lower and concentrating the cooled aqueous extract;
   (c) extracting the concentrated aqueous extract with an organic solvent, wherein the organic solvent is acetonitrile, methanol, ethanol, ethyl acetate, acetone, methyl ethyl ketone, methyl isobutly ketone, tetrahydrofuran, dioxane, or a mixture thereof to provide an organic solvent layer;
   (d) concentrating the organic solvent layer to provide a concentrated liquid and subsequently drying the concentrated liquid to obtain a crude tea extract;
   (e) dissolving the crude tea extract in a 5 to 15% aqueous methanol solution to provide an aqueous methanol extract and adding the aqueous methanol extract to a crosslinked styrenic synthetic adsorption resin, washing the synthetic adsorption resin with 5 to 15% aqueous methanol to wash out unadsorbed components;
   (f) eluting and recovering a tea catechin fraction with a 35 to 45% aqueous methanol solution, wherein the recovery of the tea catechin fraction starts at a time when the content of (−)-EGCg has reached a level twice or more as high as that of (−)-EGC and ends at a time when the content of (−)-EGCg has reached a level lower than that of (−)-ECg, or at a time when the content of caffeine becomes 5%; and
   (g) concentrating and drying the tea catechin fraction to provide the tea polyphenol composition.

2. The tea polyphenol composition according to claim 1, wherein (EGCg+GCg) are together present in the polyphenol composition in an amount between 65 wt % to 80 wt %.

3. The tea polyphenol composition according to claim 1, wherein a wt % ratio of (EGCg+GCg) to (EC, C, EGC, GC, ECg, and Cg) is between 2 and 4.

4. The tea polyphenol composition according to claim 1, wherein a wt % ratio of (EGCg+ECg+GCg+Cg) to (EC+EGC+GC+C) is between 3 and 7.

5. The tea polyphenol composition according to claim 1, wherein a wt % ratio of (EGCg+GCg) to (EC+EGC+GC+C) is between 2 and 6.

6. The tea polyphenol composition according to claim 1, wherein (GCg+GC+Cg+C) are together present in the polyphenol composition in an amount between 2 wt % to 15 wt %.

7. The tea polyphenol composition according to claim 1, wherein a wt % ratio of EGCg to (EC+EGC+ECg) is between 2 and 4.

8. The tea polyphenol composition according to claim 1, further comprising caffeine in an amount between 0.0001 wt % and 1.2 wt %.

9. The tea polyphenol composition according to claim 1, further comprising ash in an amount between 0.0001 wt % and 0.2 wt %.

10. The tea polyphenol composition according to claim 1, wherein gallic acid is not present in measurable quantities.

11. A tea polyphenol composition, comprising:
    a plurality of at least seven distinct catechins, wherein the catechins are selected from the group consisting of EGCg, GCg, EC, C, EGC, GC, ECg, and Cg; wherein
    (I) EGCg and GCg are together present in the polyphenol composition in an amount between 65 wt % to 80 wt %;
    (II) a wt % ratio of (EGCg+GCg) to (EC, C, EGC, GC, ECg, and Cg) is between 2 and 4;
    (III) a wt % ratio of (EGCg+ECg+GCg+Cg) to (EC+EGC+GC+C) is between 3 and 7;
    (IV) a wt % ratio of (EGCg+GCg) to (EC+EGC+GC+C) is between 2 and 6;
    (V) (GCg+GC+Cg+C) are together present in the polyphenol composition in an amount between 2 wt % to 15 wt %; and
    (VI) a wt % ratio of EGCg to (EC+EGC+ECg) is between 2 and 4.

12. The tea polyphenol composition according to claim 11, further comprising caffeine in an amount between 0.0001 wt % and 1.2 wt %.

13. The tea polyphenol composition according to claim 11, further comprising ash in an amount between 0.0001 wt % and 0.2 wt %.

14. The tea polyphenol composition according to claim 11, wherein gallic acid is not present in measurable quantities.

* * * * *